(12) United States Patent
Mehta et al.

(10) Patent No.: US 6,602,896 B1
(45) Date of Patent: Aug. 5, 2003

(54) P38$^{MAPK}$ INHIBITOR AND USES THEREOF

(75) Inventors: Kamal D. Mehta, Little Rock, AR (US); Rajesh P. Singh, Lukhnow (IN)

(73) Assignee: The Board of Trustees of the University of Arkansas, Little Rock, AR (US)

( * ) Notice: Subject to any disclaimer, the term of this patent is extended or adjusted under 35 U.S.C. 154(b) by 0 days.

(21) Appl. No.: 09/539,584

(22) Filed: Mar. 31, 2000

Related U.S. Application Data

(60) Provisional application No. 60/127,343, filed on Apr. 1, 1999, now abandoned.

(51) Int. Cl.$^7$ .................... A61K 31/415; A61K 31/44; A61K 31/435
(52) U.S. Cl. ................ 514/397; 514/396; 514/343; 514/340; 514/336; 514/277; 514/279; 514/385; 514/387
(58) Field of Search ................. 514/277, 279, 514/385, 387, 397, 396, 343, 340, 336

(56) References Cited

PUBLICATIONS

Kumar et al., Journal of Biological Chemistry, (Jun. 19, 1998) vol. 273, No. 25, pp. 15742–15748.*

Kumar et al., Journal of Lipid Research, (Nov., 1997) vol. 38, No. 11, pp. 2240–2248.*

* cited by examiner

*Primary Examiner*—Sreeni Padmanabhan
*Assistant Examiner*—S. Jiang
(74) *Attorney, Agent, or Firm*—Benjamin Aaron Adler

(57) ABSTRACT

The present invention demonstrates that p38$^{MAPK}$ inhibitor induces low density lipoprotein receptor expression 6–8 fold, and further provides the application of such inhibitor in the treatment of hypercholesterolemia.

5 Claims, 10 Drawing Sheets

| SB202190 | − | + | + | + | + | + | + | + |
|---|---|---|---|---|---|---|---|---|
| PD98059 | − | − | − | − | − | − | − | + |
| Time (h) | 0 | .16 | .33 | .66 | 1 | 4 | 16 | .33 |

← p42/44$^{MAPK}$

| SB202190 | − | + | + |
|---|---|---|---|
| PD98059 | − | − | + |

← LDL Receptor

P38$^{MAPK}$ INHIBITOR AND USES THEREOF

CROSS-REFERENCE TO RELATED APPLICATION

This non-provisional patent application claims benefit of provisional patent application U.S. Ser. No. 60/127,343, filed Apr. 1, 1999, now abandoned.

FEDERAL FUNDING NOTICE

The present invention was funded in part by National Institute of Health (Grant HL-51592-04). Consequently, the United States government has certain rights in this invention.

BACKGROUND OF THE INVENTION

1. Field of the Invention

The present invention relates generally to the fields of molecular biology and protein biochemistry. More specifically, the present invention relates to p38$^{MAPK}$ inhibitor(s) and applications of p38$^{MAPK}$ inhibitor(s) in the treatment of hypercholesterolemia.

2. Description of the Related Art

Mitogen-activated protein kinases (MAPKs) are proline-directed serine-threonine-protein kinases that have important functions as mediators of cellular responses to a variety of extracellular stimuli (1–4). Three subgroups of the mitogen-activated protein kinase super-family have been clearly identified: the extracellularly responsive kinases (p42/44$^{MAPK}$ or ERK-1/2), the c-Jun N-terminal kinases (p46/54$^{JNK}$) which are also known as the stress-activated protein kinases (SAPK), and the p38$^{MAPK}$ (also known as RK, Mxi-2, CSBP1/2 or HOG-1-related kinases).

Although the mitogen-activated protein kinase families are structurally related, they are generally activated by distinct extracellular stimuli through distinct upstream dual specificity kinases, thus comprising a series of separate mitogen-activated protein kinase cascades (5–7). The best known pathway, Raf/MAPK/ERK kinase-1/2 (MEK-1/2)/p42/44$^{MAPK}$ is typically strongly stimulated by growth factors and mitogenic stimuli, usually by means of a Ras-Raf-1-dependent cascade (8, 9). In contrast, the other two pathways, p38$^{MAPK}$ and p46/54$^{JNK}$ are primarily activated by cellular stresses, including heat and osmotic shock, UV irradiation, proinflammatory cytokines, and hypoxia/reoxygenation (10–16). Ten isoforms of p46/54$^{JNK}$ and four/isoforms of p38$^{MAPK}$ have been identified in mammalian cells (17–26). No physiological role has been associated with the difference in substrate affinity of the JNKs or p38$^{MAPK}$. Dual specificity kinases that activate p46/54$^{JNK}$ are MAPK kinase 4 (MKK4/SEK-1) and MKK7, whereas MK3 and MKK6 have been identified as activators of p38$^{MAPK}$, displaying some degree of selectivity for individual p38$^{MAPK}$ isoforms (26–32). MKK6 functions as an activating kinase for all known p38$^{MAPK}$ isoforms, whereas MK3 predominantly activates the isoform p38$^{MAPK}$δ. Among the identified substrates of mitogen-activated protein kinases are a variety of transcription factors that become activated upon their phosphorylation (1, 4, 6, 33).

Since specific inhibitors of the p42/44$^{MAPK}$ and p38$^{MAPK}$ cascades were first described, they have been widely used to investigate their involvement in intracellular signal transduction pathways. The flavone compound PD98059 (2-(2'-amino-3'-methoxyphenyl) oxanaphthalen-4-one) is a specific inhibitor of the mammalian MEK-1/2 and has been used extensively for investigating physiological function of p42/44$^{MAPK}$ pathway (34). The pyridinylimidazole compounds SB203580 (4-(4-Fluorophenyl)-2-(4-methylsulfinylphenyl)-5-(4-pyridyl) 1H-imidazole) and SB202190 (4-(4-Fluorophenyl)-2-(4-hydroxyphenyl)-5-(4-pyridyl) 1H-imidazole) are specific inhibitors for p38$^{MAPK}$ since they selectively inhibit both p38$^{MAPK}$ α- and β-isoforms, but not the γ- and δ-isoforms. In addition, they exhibit no significant effect upon other related kinases, including other members of the mitogen-activated protein kinase families and their upstream activators (17, 35). A role for the p38$^{MAPK}$ has previously been identified using these inhibitors in diverse cellular processes such as lipopolysaccharide- and tumor necrosis factor-α (TNF)-induced cytokine production (17, 36), ultraviolet-and anisomycin-induced c-jun and c-fos expression (37), interleukin (IL)-2 and IL-7-mediated T-cell proliferation (38), glutamate- (39) and B cell Ag receptor-induced apoptosis (40), fibroblast growth factor-, arsenite and UVC-mediated CREB/ATF-1 phosphorylation (41, 42).

Analysis of the signal transduction pathways using the above inhibitors revealed a critical role for p42/44$^{MAPK}$ activation in induction of LDL receptor gene expression by a variety of extracellular stimuli (43–45).

The prior art is deficient in the lack of understanding the role of p38$^{MAPK}$ in the regulation of the LDL receptor expression. Further, the prior art is deficient in the lack of effective means of applying p38$^{MAPK}$ inhibitors to treat hypercholesterolemia. The present invention fulfills this long-standing need and desire in the art.

SUMMARY OF THE INVENTION

The present invention addresses directly the physiological role of p38$^{MAPK}$ in the regulation of LDL receptor expression by using highly specific pharmacological and molecular tools. Results presented demonstrate that simple inhibition of the p38$^{MAPK}$ basal activity is sufficient to induce LDL receptor expression. Co-transfection studies established that SB202190-induced LDL receptor expression is mediated by the activation of p42/44$^{MAPK}$ resulting from the inhibition of p38$^{MAPK}$ α-isoform. Therefore, in intact cells, p38$^{MAPK}$ negatively regulates the p42/44$^{MAPK}$ and the responses mediated by this kinase. It is speculated that cross-talk between these mitogen-activated protein kinases, which mediate the effects of numerous extracellular stimuli, could be crucial for controlling a wide array of biological processes.

In one embodiment of the present invention, there is provided a compound for inducing low density lipoprotein receptor expression, wherein the compound is a p38$^{MAPK}$ inhibitor or a compound that activates p42/44$^{MAPK}$. The representative examples of such compounds are SB202190 and SB203580.

In another embodiment of the present invention, there is provided a method of inducing LDL receptor expression in a cell by administering to the cell a compound disclosed herein. The cell is either hepatic or nonhepatic. Preferably, the compound induces the LDL receptor expression by 6–8 fold and further reduces cholesterol level in the cell.

In still another embodiment of the present invention, there is provided a method of treating an individual having hypercholesterolemia by administering a compound disclosed herein. Preferably, the compound is administered at a concentration range of from about 1 μM to about 100 μM.

Other and further aspects, features, and advantages of the present invention will be apparent from the following description of the presently preferred embodiments of the invention given for the purpose of disclosure.

BRIEF DESCRIPTION OF THE DRAWINGS

So that the matter in which the above-recited features, advantages and objects of the invention, as well as others which will become clear, are attained and can be understood in detail, more particular descriptions of the invention briefly summarized above may be had by reference to certain embodiments thereof which are illustrated in the appended drawings. These drawings form a part of the specification. It is to be noted, however, that the appended drawings illustrate preferred embodiments of the invention and therefore are not to be considered limiting in their scope.

FIG. 4 shows SB20190-induced LDL receptor expression is mediated by $p42/44^{MAPK}$ signaling cascade.

FIG. 5 shows that SB202190 induces LDL receptor expression and phosphorylation of $p42/44^{MAPK}$ in HeLa cells, and pretreatment with PD98059 inhibited SB20219-induced LDL receptor expression.

FIG. 8 shows effects of different protein kinase C inhibitors on SB202190-induced LDL receptor expression in HepG2 cells.

DETAILED DESCRIPTION OF THE INVENTION

Figure 1:
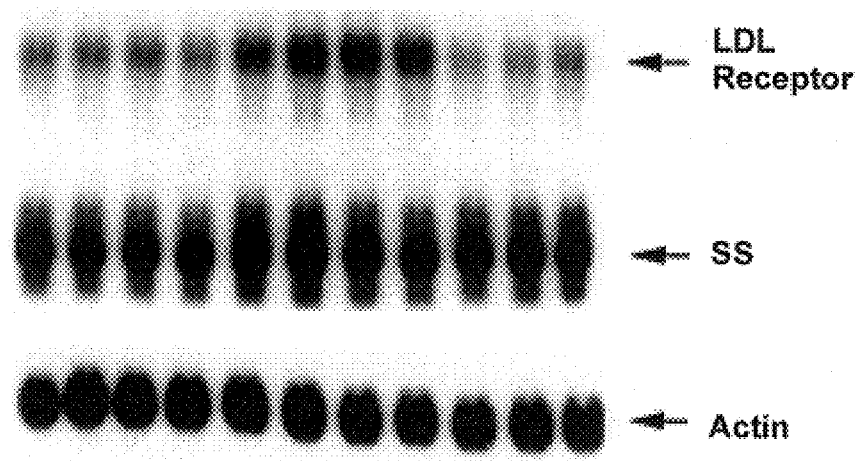
FIG. 1 shows selective induction of LDL receptor expression by SB202190. $5 \times 10^5$ cells were plated on day 0. On day 2, cells were refed with fresh medium. On day. 4, cells were either left untreated (0) or treated for the indicated times with SB202190 (2.5 µM) in medium containing 0.5% FBS. Total RNA was isolated and subjected to Northern blotting to determine amounts of LDL receptor, squalene synthase (SS) genes, and actin mRNAs. Autoradiographs were quantitated densitometrically. LDL receptor mRNA levels were normalized to actin mRNA levels. In the bottom panel, results are expressed as the fold induction by SB 202190 as compared with uninduced cells (set at 1). Values obtained are the averages of three separate experiments, with the standard deviations shown.
Figure 1:
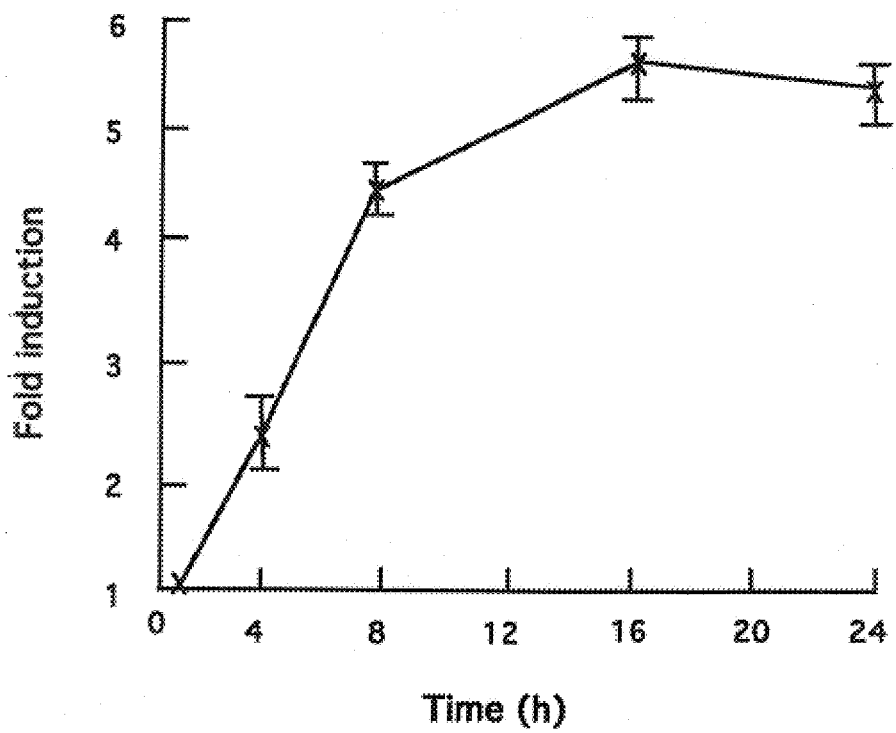

The present invention examines the role of $p38^{MAPK}$ in the regulation of the LDL receptor expression and demonstrates that there is a cross-talk between $p42/44^{MAPK}$ and $p38^{MAPK}$ signaling cascades, and $p38^{MAPK}$ negatively regulates LDL receptor expression via the $p42/44^{MAPK}$ signaling cascade.

The present invention reports that SB202190 alone, a specific inhibitor of $p38^{MAPK}$, induces low density lipoprotein (LDL) receptor expression (6–8 fold) in a sterol-sensitive manner in HepG2 cells. Consistent with this finding, selective activation of the $p38^{MAPK}$ signaling pathway by expression of MKK6b (E), a constitutive activator of $p38^{MAPK}$, significantly reduced LDL receptor promoter activity. Expression of the $p38^{MAPK}$ $\alpha$-isoform had a similar effect, whereas, expression of the $p38^{MAPK}$ $\beta$II-isoform had no effect on LDL receptor promoter activity. SB202190-dependent increase in LDL receptor expression was accompanied by induction of $p42/44^{MAPK}$ and inhibition of this pathway completely prevented SB202190-induced LDL receptor expression, suggesting that $p38^{MAPK}$ negatively regulates the $p42/44^{MAPK}$ cascade and the responses mediated by this kinase. Cross-talk between these kinases appears to be one-way because modulation of $p42/44^{MAPK}$ activity did not affect $p38^{MAPK}$ activation by a variety of stress-inducers. This cross-talk is independent of protein synthesis and clearly requires signaling in a protein kinase C-independent manner via a staurosporine-sensitive protein kinase that lies upstream of MEK1/2. Taken together, these findings reveal a hitherto unrecognized one-way communication that exists between $p38^{MAPK}$ and $p42/44^{MAPK}$ and provide the first evidence that through the $p42/44^{MAPK}$ signaling cascade, the $p38^{MAPK}$ $\alpha$-isoform negatively regulates LDL receptor expression, representing a novel mechanism of fine-tuning cellular levels of cholesterol in response to a diverse set of environmental cues.

In one embodiment of the present invention, there is provided a compound for inducing low density lipoprotein receptor expression, wherein the compound is a $p38^{MAPK}$ inhibitor or a compound that activates $p42/44^{MAPK}$. The representative examples of such compounds are SB202190 and SB203580.

In another embodiment of the present invention, there is provided a method of inducing LDL receptor expression in a cell by administering to the cell with the compound disclosed herein. The cell is either hepatic or nonhepatic. Preferably, the compound induces the LDL receptor expression by 6–8 fold and further reduces cholesterol level in the cell.

In still another embodiment of the present invention, there is provided a method of treating an individual having hypercholesterolemia by administering the compound disclosed herein. Preferably, the compound is administered at a concentration range of from about 1 $\mu$M to about 100 $\mu$M.

The following examples are given for the purpose of illustrating various embodiments of the invention and are not meant to limit the present invention in any fashion.

EXAMPLE 1

Materials

Cycloheximide, calphostin C, PD98059, and SB202190 were purchased from Calbiochem (San Diego, Calif.). Phospho-specific antibodies to the activated forms of $p42/44^{MAPK}$ (Thr 202/Tyr 204), $p46/54^{JNK}$ (Thr 183/Tyr 188), $p38^{MAPK}$ (Thr 180/Tyr 182), and MEK1/2(Ser 217/221) were purchased from New England Biolabs (Beverly, Mass.). Antibodies to $p42/44^{MAPK}$, mitogen-activated protein kinase phosphatase-1 (MKP-1) were obtained from Santa Cruz Biotechnology (Santa Cruz, Calif.). IL-1$\beta$ and TNF were purchased from R & D Systems Inc. (Minneapolis, Minn.). TRIzol and all tissue culture supplies were from Life Technologies Inc. (Gaithersburg, Md.). Zeta probe blotting membrane and the protein assay reagent were purchased from Bio-Rad (Hercules, Calif.). [$\alpha$-$^{32}$P]dCTP (3000 Ci/mmol) was obtained from Dupont (Boston, Mass.), and the enhanced chemiluminescence (ECL) detection kit was obtained from Amersham International (Arlington Heights, Ill.). pSV-$\beta$-galactosidase (pSV-$\beta$-Gal) vector was purchased from Promega, and was used as a positive control for monitoring transfection efficiencies of HepG2 cells (24). Dual-Light chemiluminescent reporter gene assay system for the combined detection of luciferase and 6-galactosidase was purchased from TROPIX, Inc.

EXAMPLE 2

Cell Culture

Human hepatoma cell line HepG2 and its derivative HepG2-$\Delta$Raf-1:ER cell line that stably expresses the $\Delta$Raf-1:ER chimera were maintained as monolayer cultures in a humidified 5% $CO_2$ atmosphere at 37° C. in Eagle's minimum essential medium (EMEM) (Bio Whittaker, Md.) supplemented with 10% fetal bovine serum (FBS) (Life Technologies Inc.), 2 mM L-glutamine, 20 units/ml penicillin and 20 $\mu$g/ml streptomycin sulphate.

EXAMPLE 3

Immunoblot Analysis

Proteins were fractionated by SDS-PAGE with an 10% acrylamide separation gel, and the separated proteins were transferred to nitrocellulose, and processed as described previously (43, 44). Briefly, membranes were incubated in 20 mM Tris-HCl, pH 7.6, 137 mM NaCl, 0.2% v/v Tween-20 (Tris/NaCl/Tween-20) with 5% w/v non-fat dried milk for 1 h, washed in Tris/NaCl/Tween-20 (3×5 min), and incubated for 1 h with primary antibody in Tris/NaCl/Tween-20 containing 1% milk at room temperature for non phospho-specific antibodies and overnight at 4° C. for phospho-specific antibodies. The following dilutions were used for individual antibodies against different proteins: $p_{42/44}{}^{MAPK}$ (1:1600); phosphop-42/44$^{MAPK}$ (1:1000); phosphop-46/54$^{JNK}$ (1:1000); phospho-p38$^{MAPK}$ (1:1600); phospho-MEK-1/2 (1:1000); MKP-1 (1:1500). After further washing in Tris/NaCl/Tween-20, membranes were incubated for 1 h with horseradish peroxidase-linked anti-IgG secondary antibody (Bio-Rad, diluted 1:5000), and immunoreactive proteins were detected by ECL as described by the supplier. Quantitative analyses of protein levels were performed by densitometric scanning of the autoradiograms, and are representative of 3 or more independent experiments.

EXAMPLE 4

Northern Analysis

Total RNA was isolated using TRIzol, and Northern blotting was done essentially as described earlier (43, 44). Briefly, 20 µg total cellular RNA was fractionated on 1% formaldehyde agarose gel and transferred to Zeta Probe membrane by capillary blotting. RNA blots were hybridized with LDL receptor and squalene synthase specific single-stranded M13 probes labeled with [$\alpha$-$^{32}$P]dCTP. Hybridized filters were washed and exposed to Kodak X-ray film. The relative intensities of specific bands were determined densitometrically within the linear range of the film on a model 300A laser densitometer (Molecular Dyanamics, Calif.) with Image Quant software. LDL receptor mRNA was normalized to squalene synthase (SS) (included in this study) or to $\alpha$-actin (data not shown) mRNA level, and data for each point were plotted as the percentage of LDL receptor mRNA as compared to controls.

EXAMPLE 5

Expression Vectors and Reporter Constructs

Expression vectors of MKK6b, MKK6b(E) (a double mutant of MKK6b in which serine$^{207}$ and threonine$^{211}$ are replaced with glutamic acid), MKK6 b(A) (a mutant of MKK6 b in which serine$^{222}$ is replaced with alanine), p38$^{MAPK}$ $\alpha$, p38$^{MAPK}$ $\alpha$(AF) (a double mutant of p38$^{MAPK}$ $\alpha$-isoform in which threonine$^{188}$ and tyrosine$^{190}$ with phenylalanine), and p38$^{MAPK}$ II have been described elsewhere (19, 26). Reporter gene of LDL receptor promoter-luciferase (plasmid A), in which the 5'-flanking region of human LDL receptor promoter was fused to firefly luciferase gene has also been described previously (45, 46).

EXAMPLE 6

Transient Transfection and Luciferase Assay

HepG2 cells were transfected by the Lipofectamine method. For the LDL receptor promoter-luciferase expression assays, HepG2 cells were seeded at a density of 1×10$^6$ cells per 6-well plates and co-transfected with 0.25 µg of relevant expression vector, or the corresponding empty vector (45, 46). Luciferase activity was measured 12–18 h after transfection. Normalization was achieved by co-transfecting 0.1 µg of pSV-β-Gal, a β-galactosidase reporter construct as an internal control for the transfection efficiency. Luciferase and β-palactosidase activities were measured according to the TROPIX protocol. Data are representive for at least three independent experiments performed in duplicate and are expressed as "fold increase in luciferase activity," which was calculated relative to the basal level of L receptor promoter reporter activity (set to 1 unit) and corrected for empty vector effects for each expression vector.

EXAMPLE 7

The Specific p38$^{MAPK}$ inhibitor SB202190 by Itself Induces LDL Receptor Expression To examine whether the p38$^{MAPK}$ is involved in regulation of LDL receptor expression, the effects of inhibition of this kinase was first examined by using a specific inhibitor. The activity of p38$^{MAPK}$ was inhibited by using SB202190, a highly selective inhibitor of p38$^{MAPK}$ that does not affect the activity of other relevant kinases, even at high concentrations. HepG2 cells were treated with SB202190 for various times and the effect on LDL receptor expression was measured by Northern blotting. SB202190 induces LDL receptor expression in a time-dependent manner without significantly affecting expression of a house-keeping actin gene or another sterol-sensitive gene of the cholesterol biosynthetic pathway, SS (FIG. 1). A significant increase in LDL receptor expression was apparent at 4 h and a plateau was reached after 8 h treatment of SB202190. Another specific p38$^{MAPK}$ inhibitor SB203580 also induced LDL receptor expression, whereas the inactive derivative SB202474 did not induce LDL receptor expression (data not shown). The most effective concentrations were 2.5 µM for SB202190 and 10 µM for SB203580.

Figure 2:
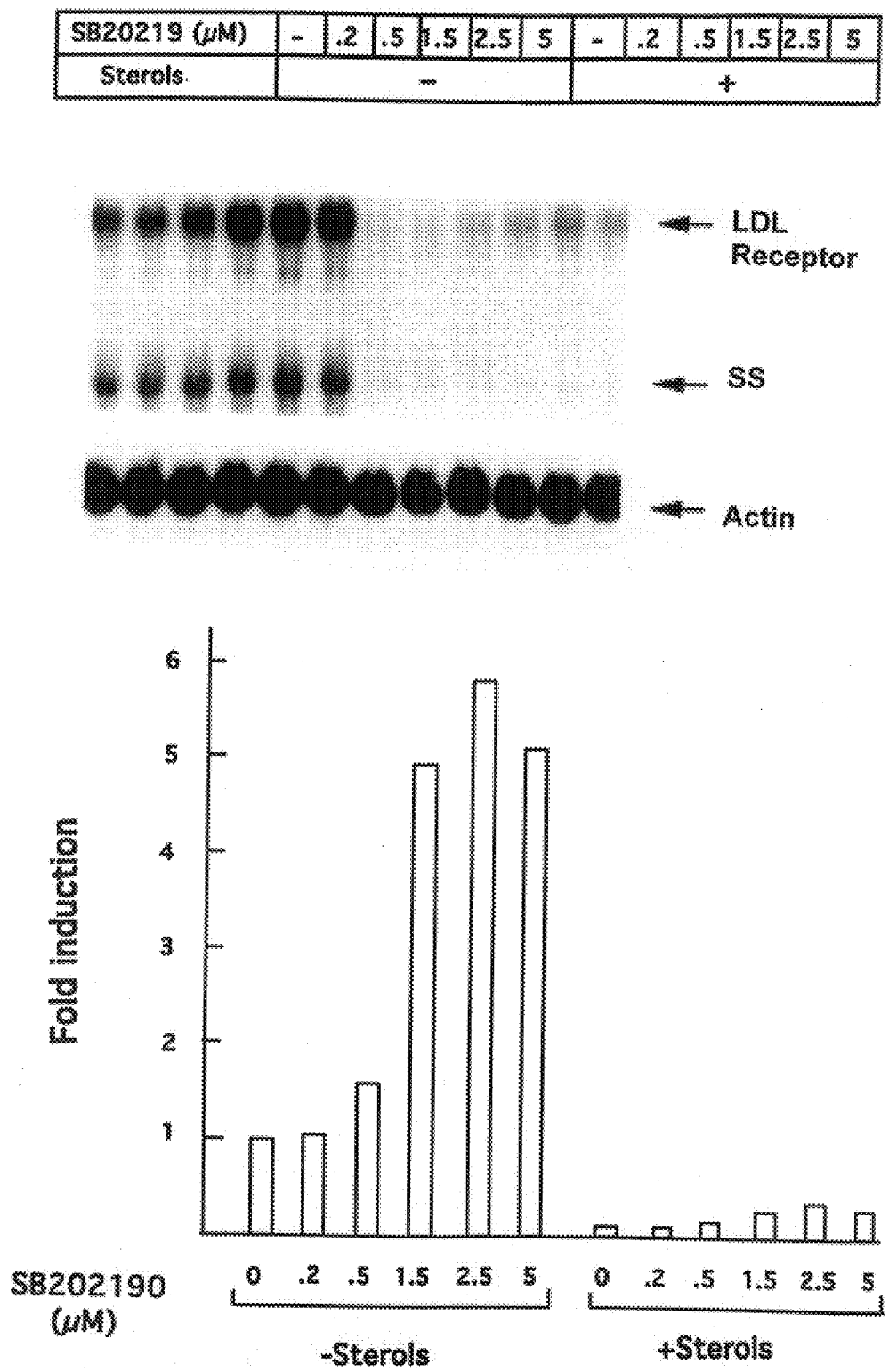
FIG. 2 shows that SB202190 induces LDL receptor expression in a sterol-sensitive manner irrespective of concentrations. HepG2 cells were grown as described in FIG. 1. On day 4, medium was changed to either 10% LPDS alone or 10% LPDS supplemented with 25-hydroxycholesterol (2 µg/ml) and cholesterol (10 µg/ml), and after 2 hours, cells were treated with indicated concentrations of SB202190 for an additional 4 hours. Levels of LDL receptor and SS mRNAs were determined by Northern analysis and densitometry as described previously. RNA levels were normalized by comparison with levels of actin. Values obtained from cells cultured in the absence of sterols and SB202190 were set at 1. Values shown are the average of two different experiments. The experiment was repeated two times with similar results.

Because LDL receptor is negatively regulated by sterols, whether SB202190 can induce LDL receptor expression in the presence of sterols was then tested. As shown in FIG. 2, presence of sterols suppressed SB202190-induced LDL receptor expression. However, a slight increase in the suppressed levels of LDL receptor was observed in a dose-dependent manner on treatment with SB202190.

Because pyridinyl imidazoles that are closely related to SB203580 have cyclooxygenase-inhibitory activity (47, 48), experiments were conducted to determine whether blockade of this activity with indomethacin (49) can alter LDL receptor expression. Importantly, unlike SB202190, 10 µM indomethacin did not significantly alter LDL receptor expression (results not shown).

From the above data, it seemed probable that the effect of SB202190 on LDL receptor expression is related to its inhibition of P38$_{MAPK}$.

EXAMPLE 8

The p$_{38}{}^{MAPK}$ Pathway Negatively Regulates LDL Receptor Expression

Figure 3:
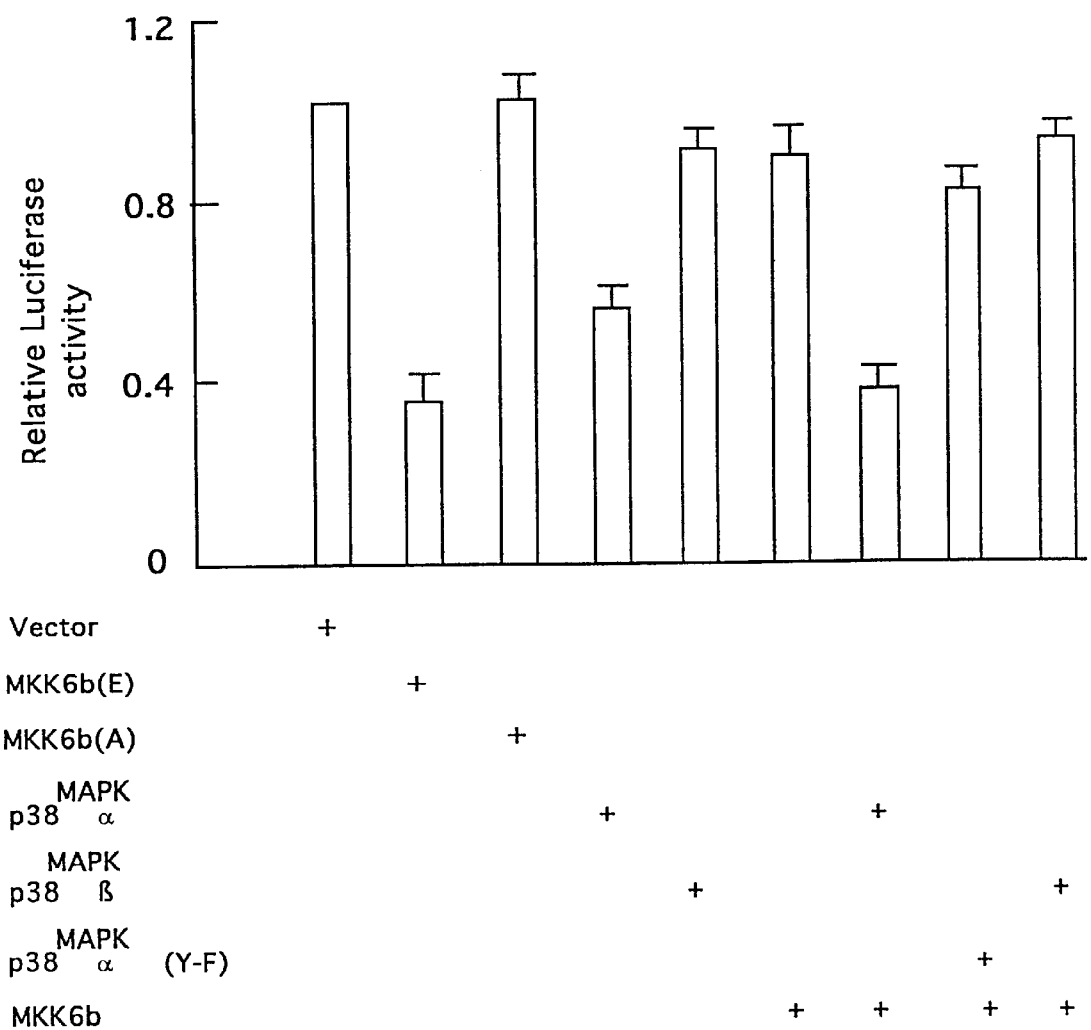
FIG. 3 shows activation of $p38^{MAPK}$ α-isoform interferes with LDL receptor promoter activity. (A) HepG2 cells were co-transfected with LDL receptor-luciferase reporter (plasmid A) (46) and expression vectors encoding MKK6b, MKK6b(A), MKK6b(E), $p38^{MAPK}$ α-isoform, $p38^{MAPK}$ β-isoform, $p38^{MAPK}$ α-isoform (AF) as indicated. Following transfection, cells were washed three times with PBS and maintained in 0.5% FBS. After 16 hours, cells were harvested and luciferase activity was determined and normalized to the protein content of each extract. Luciferase activity expressed by cells transfected with empty vector was given an arbitrary value of 1. The results are presented as means ±standard errors and represent at least four individual experiments. The amount of DNA used were: plasmid A (0.75 µg/well), MKK6b, MKK6b(A), MKK6b (E) (0.6 µg/well), $p38^{MAPK}$ α-isoform, α(AF) mutant, $p38^{MAPK}$ β-isoform (0.2 µg/well).

To investigate the role of p38$^{MAPK}$ signaling pathway in the regulation of LDL receptor expression more directly, previously characterized expression constructs was used to modulate either positively or negatively the endogenous p38$^{MAPK}$ activity. LDL receptor transcription was monitored by transfecting HepG2 cells with a previously cloned fragment of the human LDL receptor promoter fused to the luciferase reporter gene (46), together with the relevant constructs. In several cell systems, p38$^{MAPK}$ activity can be stimulated by coexpression of p38$^{MAPK}$ with MKK6b, or by expression of constitutively activated MKK6b(E), in which the activating phosphorylation residues Ser207 and Thr211 were replaced by glutamic acids (19, 50). Expression of MKK6b(E) reduced luciferase gene expression many fold, when compared with the luciferase expression in control cells transfected with the empty vector (FIG. 3). This dramatic down-regulation of the LDL receptor reporter expression in cells overexpressing the constitutively active MKK6b mutant most likely resulted from a decrease in p42/44$^{MAPK}$ activity in these cells, as assessed by measuring activity of the co-transfectedp 42/44$^{MAPK}$ plasmid (FIG. 3). Conversely, expression of the dominant-negative regulatory MKK6b(A) construct slightly increased LDL receptor-luciferase expression, correlating with a partial inhibition of endogenous MKK6b activity in cells expressing this mutated form of MKK6b.

To rule out the possibility that MKK6b(E) may suppress LDL receptor promoter activity in a p38$^{MAPK}$-independent manner, it was tested whether MKK6b(E)-inhibited lDL receptor expression was due to activation of p38$^{MAPK}$. HepG2 cells were transfected with the human LDL receptor promoter-luciferase reporter gene along with expression vectors encoding p38$^{MAPK}$ α or β(βII)-isoform, MKK6b, or empty vector. It is interesting to note that expression of p38$^{MAPK}$ α-isoform or with MKK6b alone was able to suppress reporter gene expression mildly. However, coexpression of p38$^{MAPK}$ α-isoform and MKK6b together strongly reduced luciferase activity many fold (FIG. 3). The effect of MKK6b is dependent on p38$^{MAPK}$ activation, since. MKK6b failed to stimulate reporter gene activity when it was co-transfected with an inactive p38$^{MAPK}$ α(AF) mutant, in which one of the activating phosphorylation residues, Tyr 182, was replaced by phenylalanine. At the same time, transfection of p38$^{MAPK}$ β-isoform alone or with MKK6b had no significant effect. These results demonstrate that activation of p38$^{MAPK}$ by itself is sufficient to suppress reporter gene expression. Furthermore, it is concluded that p38$^{MAPK}$ α-isoform and not p38$^{MAPK}$ α-isoform mediates SB202190-induced LDL receptor expression.

EXAMPLE 9

SB202190-Induced LDL Receptor Expression is Mediated by p42/44$^{MAPK}$ Signaling Cascade Since p42/44$^{MAPK}$ have been shown to play a critical role in induction of LDL receptor expression (43–45), it is determined whether inhibition of p38$^{MAPK}$ by SB202190 leads to activation of other mitogen-activated protein kinases,p 42/44$^{MAPK}$ and p46/54$^{JNK}$. HepG2 cells were incubated with SB202190, and the activity of p42/44$^{MAPK}$ and p$_{46/54}$$^{JNK}$ was determined by immunoblot analysis with antibodies that recognized the activated phosphorylated forms of these kinases in cell extracts obtained at different times.

Figure 4A:
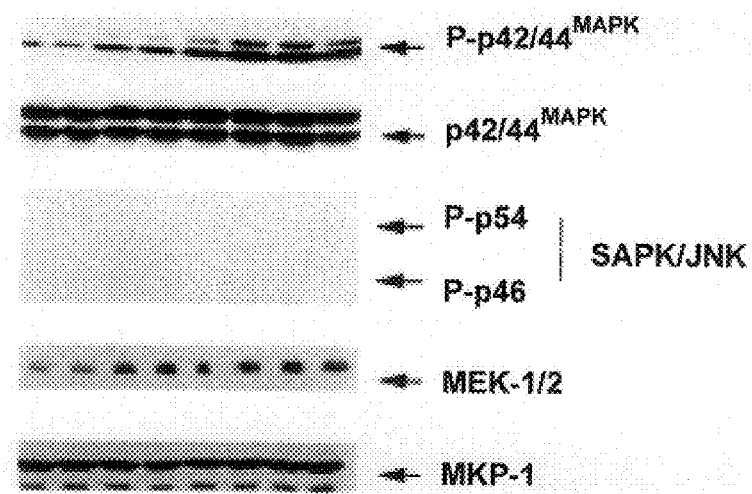
FIG. 4A shows kinetics of $p42/44^{MAPK}$, and MEK-1/2 activation by SB202190. $2 \times 10^5$ cells were grown and treated as described in FIG. 1. After the indicated times, equal amounts of cell lysates were blotted with anti-phospho-$p42/44^{MAPK}$ antibody, phosphorylation-independent $p42/44^{MAPK}$ antibody, anti-phospho $p46/54^{JNK}$ antibody, anti-phospho-MEK-1/2, or phosphorylation-independent MKP-1.
Figure 4C:
FIG. 4C shows that cells were grown as described in FIG. 2. On day 4, medium was changed to either 10% LPDS alone or 10% LPDS supplemented with three different concentrations of 25-hydroxycholesterol (2 µg/ml, 5 µg/ml, or 10 g/ml) together with cholesterol (10 µg/ml). After 2 h, cells were treated with 2.5 µM SB202190 for an additional 4 h. Cell extracts were prepared, and equal amounts were subjected to SDS-PAGE and immunoblotted with anti-phospho-$p42/44^{MAPK}$, or phosphorylation-independent anti-$p42/44^{MAPK}$. Results shown are indicative of three separate experiments.
Figure 4B:
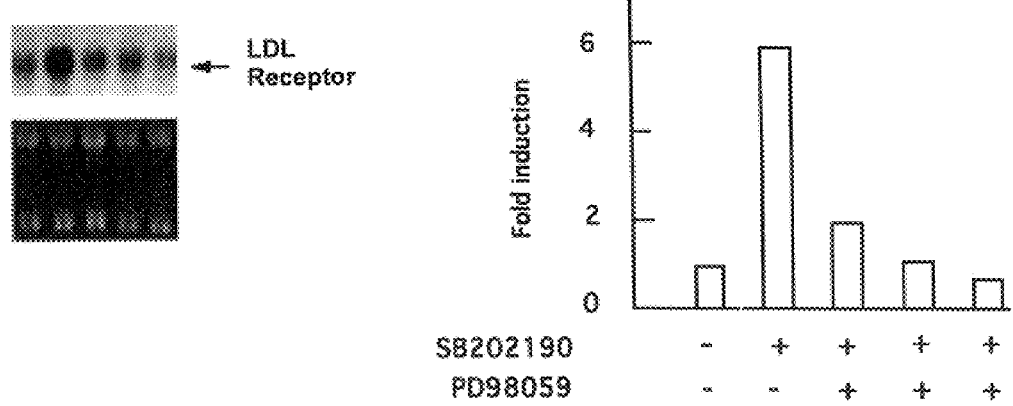
FIG. 4B shows that HepG2 cells were grown as described in FIG. 1, and were either untreated or treated with SB202190 (2.5 µM) for 4 h either in the absence or presence of indicated concentrations of PD98059 that was added 30 min prior to SB202190 (2.5 µM) addition. Total RNA was subjected to Northern blot analysis, and the filter was hybridized with a $^{32}$P-labeled LDL receptor probe. Values shown are the averages of two different experiments. Ethidium bromide staining of RNA gel before blotting onto a nitrocellulose to demonstrate equal loading of RNA in all lanes. Values obtained from the control cells grown in the absence of SB202190 or PD98059 were arbitrarily set at 1.

In contrast to the rapid and transient growth factor-induced activation of p42/44$^{MAPK}$, SB202190 treatment caused a delayed and prolonged activation with no effect on p42/44$^{MAPK}$ protein levels (FIG. 4A). Weak activation was observed at 1 hour after treatment, and maximal activation was obtained at 4–8 hours after stimulation. The activated p42/44$^{MAPK}$ remained elevated at least until 24 hours, the maximum time point measured. Furthermore, changes in p42/44$^{MAPK}$ activity took place with little or no effect on the activity or levels of p46/54$^{JNK}$ (FIG. 4A). Because the kinetics of MEK-1/2 phosphorylation paralleled the appearance of p42/44$^{MAPK}$, it is likely that MEK-1/2 is upstream of p42/44$^{MAPK}$. Because MEK-1/2 directly phosphorylates and activates p42/44$^{MAPK}$, PD98059 was used to determine the role of this pathway in SB202190-induced LDL receptor expression. PD98059 inhibited both SB202190-induced p42/44$^{MAPK}$ phosphorylation (FIG. 4B) and induction of LDL receptor expression, suggesting that LDL receptor induction is mediated by SB202190-dependent p42/44$^{MAPK}$ activation. Furthermore, lack of effect of sterols on SB202190 induced p42/44$^{MAPK}$ phosphorylation ruled out involvement of a sterol-sensitive step in p42/44$^{MAPK}$ activation (FIG. 4C). These results suggested that p38$^{MAPK}$ negatively regulates p42/44$^{MAPK}$ activity and the SB202190-dependent increase in LDL receptor expression is mediated by p42/44$^{MAPK}$.

Figure 5A:
FIG. 5A shows that $1 \times 10^5$ cells were plated on day 0, and were refed with fresh medium on day 2. On day 4, cells were treated with SB202190 (2.5 µg/ml) in 0.5% FBS. After the indicated times, cells were lysed in SDS sample buffer, and subjected to Western blotting with anti-phospho-$p42/44^{MAPK}$ or phosphorylation-independent anti-$p42/44^{MAPK}$. Equal amounts of $p38^{MAPK}$ was observed in all the lanes (data not shown).
Figure 5B:
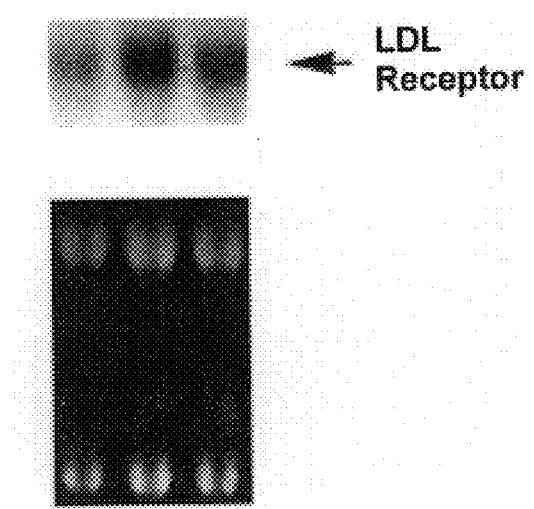
FIG. 5B shows that HeLa cells were either untreated or treated with SB202190 (2.5 µM) for 4 h either in the absence or presence of of PD98059 (5 µM). PD98059 was added 30 min prior to addition of SB202190. After the indicated times, total RNA was isolated and subjected to Northern blotting. RNA gel stained with ethidium bromide before blotting onto nitrocellulse is shown t o demonstrate equal loading of RNA.

It was then tested whether p38$^{MAPK}$ inhibition by SB202190 induces LDL receptor expression in other cell types. In HeLa cells, SB202190 treatments induced p42/44$^{MAPK}$ activity and caused a increase in LDL receptor expression (FIG. 5). One interesting feature is the delayed and sustained kinetics of p42/44$^{MAPK}$ activation by SB202190 in HepG2 cells as compared to rapid and transient kinetics of p42/44$^{MAPK}$ increase in non-hepatic HeLa cells (FIG. 5). It is possible that the differences in the kinetics and extents of stimulation of p42/44$^{MAPK}$ activity and LDL receptor induction may reflect the underlying differences between these cell types. Inspite of these differences, consistent with the role of p42/44$^{MAPK}$, PD98059 blocked SB202190-induced LDL receptor expression.

EXAMPLE 10

Modulation of Endogenous p42/44$^{MAPK}$ Activity does not Affect p38$^{MAPK}$ Activation Whether inhibition or activation of p42/44$^{MAPK}$ regulates p38$^{MAPK}$ activation by stress-inducers was determined next. To test this possibility, a HepG2-derived cell line (HepG2ΔRaf:ER) expressing an estradiol-dependent human Raf-1 protein kinase was generated. In this cell line, the ΔRaf-1:ER chimera is activated in response to estradiol or anti-estrogen ICI 182780, thereby activating MEK-1/2 and then p42/44$^{MAPK}$ (51, 52).

Figure 6:
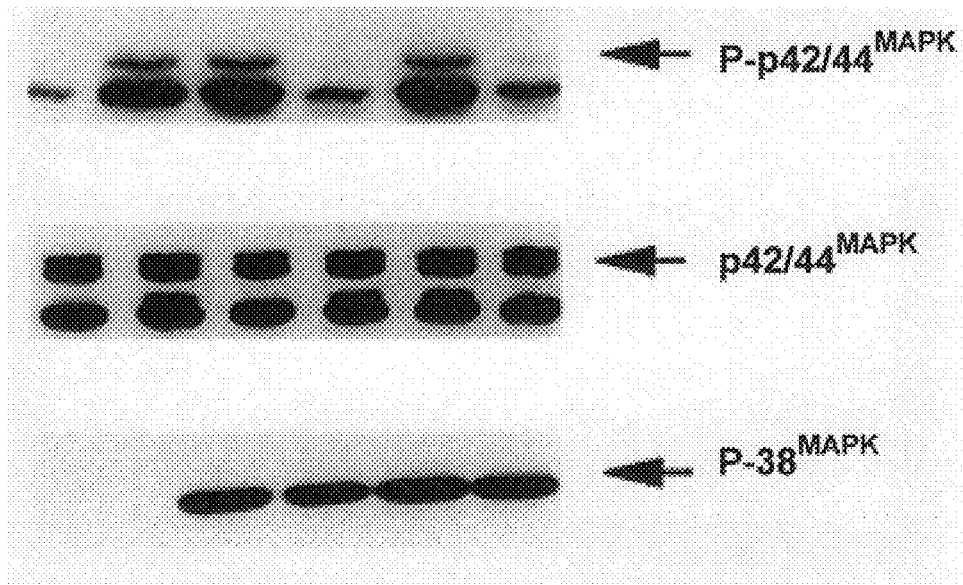
FIG. 6 shows modulation of $p_{42/44}^{MAPK}$ activity does not affect $p38^{MAPK}$ phosphorylation in response to a variety of stress-inducers in HepG2-ΔRaf-1:ER cells. Cells were either left untreated or stimulated with 1 µM ICI 182,780 for 1.5 h, and then treated with either anisomycin (50 ng/ml) or IL-1β(5 ng/ml) for 30 min. Cells were then lysed in SDS sample buffer, and equal amounts of whole cell lysates were separated by SDS-PAGE in 10% gels. Activated MAPKs levels were analyzed by blotting using anti-phospho-$p42/44^{MAPK}$, and anti-phospho-$p38^{MAPK}$. Protein levels were analyzed by using phosphorylation-independent anti-$p42/44^{MAPK}$ following electrotransfer of total proteins onto nitrocellulose. Similar results were obtained in three separate experiments.

Addition of ICI 182780 to these cells stimulated p42/44$^{MAPK}$ within minutes (FIG. 6). The p42/44$^{MAPK}$ activity increased for up to 1 h, and remained elevated in the presence of ICI 182780. This cell system was used to directly measure the effect of ICI 182780 on p38$^{MAPK}$ activation by a variety of stress-inducers. As shown in FIG. 6, no significant effects was observed on p38$^{MAPK}$ activation by anisomycin or IL-1β on super-induction of p42/44$^{MAPK}$ activity with ICI 182780. Likewise, inhibition of p42/44$^{MAPK}$ with PD98059 has no effect on activity of other MAPKs (data not shown). This is consistent with earlier demonstration that PD98059 failed to block p38$^{MAPK}$ activation in response to IL-1β or TNF at concentrations that completely blocked p42/44$^{MAPK}$ activation by MEK-1/2 (43). Similar results have also been obtained by Frasch e t al. in human neutrophils (53). Collectively, the above results demonstrate that p42/44$^{MAPK}$ does not regulate p38$^{MAPK}$ activation by a variety of transcriptional modulators.

EXAMPLE 11

Figure 7:
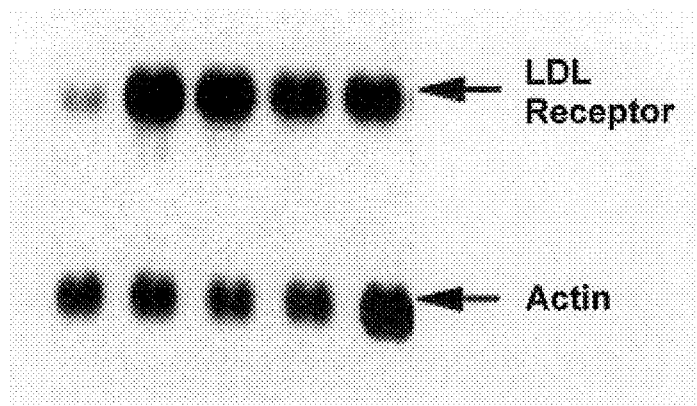
FIG. 7 shows that SB202190-induced LDL receptor expression does not require new protein synthesis. HepG2 cells were grown as described in FIG. 1. On day 4, cells cultured for 1 h in 0.5% FBS containing different amounts of cycloheximide (1 µg/ml, 2 µg/ml, and 5 µg/ml) were then incubated with SB202190 (2.5 µM) for an additional 4 h. LDL receptor and actin mRNA levels were analyzed by Northern blotting of total RNA. Values obtained from cells with no additions were arbitrarily set at 1. The experiment was repeated two times with similar results. Results shown are representative of one experiment.
Figure 7:
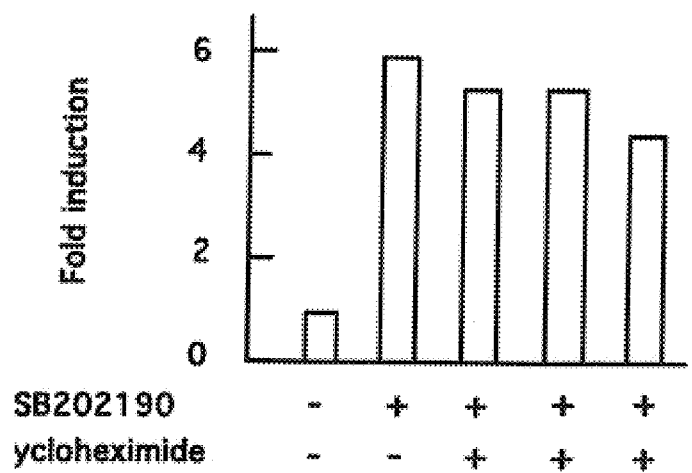

SB202190-Induced LDL Receptor Expression is Independent of New Protein Synthesis To determine whether the induction of LDL receptor expression by SB202190 may require new protein synthesis, HepG2 cells were incubated with SB202190 in the absence or presence of different concentrations of cycloheximide. Data shown in FIG. 7 demonstrates that inhibition of translation has no effect on LDL receptor expression, suggesting that an additional protein synthesis is not required to stimulate LDL receptor expression.

EXAMPLE 12

Involvement of a Staurosporine-sensitive Step in SB202190-Induced p$_{42/44}$$^{MAPK}$ Activation and Induction of LDL Receptor Expression There may be several pathways leading to p42/44$^{MAPK}$ activation. Protein kinase C (PKC) is implicated in at least one of them because phorbol-ester, a well-known activator of protein kinase C, activates p42/44$^{MAPK}$ and inhibitors of protein kinase C prevent agonist-induced p42/44$^{MAPK}$ activation in several types of cells (44).

Figure 8A:
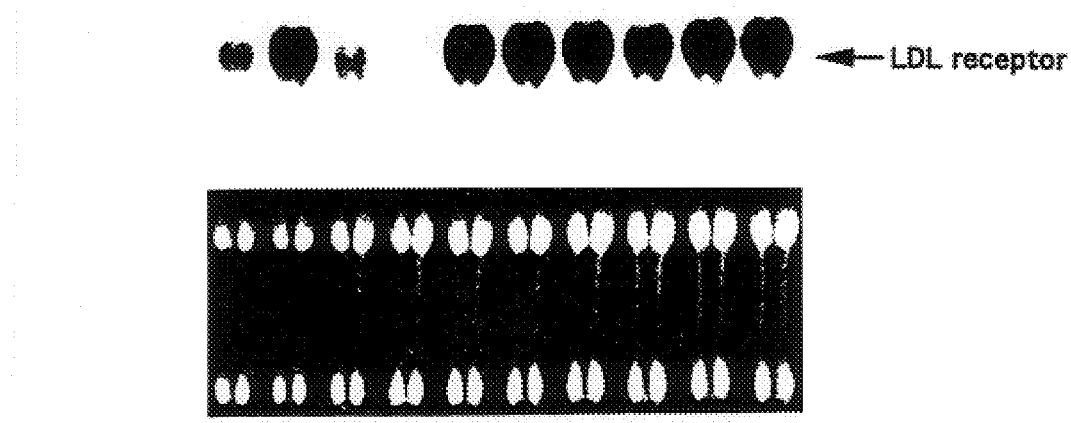
In FIG. 8A, HepG2 cells were pretreated for 30 minutes with the indicated concentration of the above inhibitors and then treated with 2.5 FM SB202190 for an additional 4 hours. Total RNA was subjected to Northern blotting for measurement of LDL receptor mRNA levels. Ethidium bromide staining of RNA gel before blotting onto a nitrocellulose paper to demonstrate equal loading of RNA in all lanes. Similar results were obtained in four seaparate experiments.
Figure 8B:
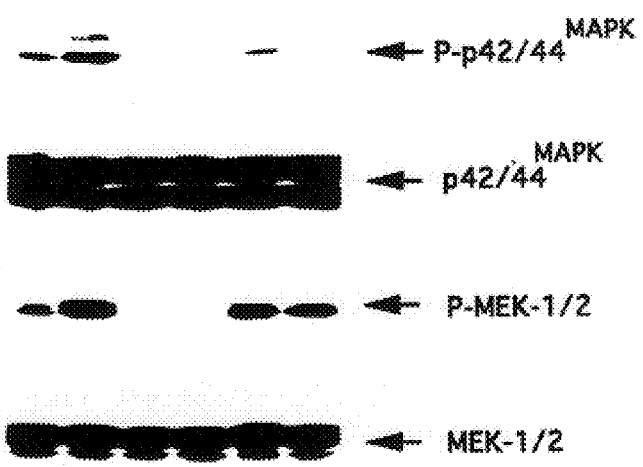
FIG. 8B shows that staurosporine blocked SB202190-induced $p42/44^{MAPK}$ and MEK-1/2 activation. HepG2 cells were cultured in the absence or presence of 1 $\mu$M staurosporine or 5 $\mu$M PD98059 for 30 min. SB202190 (2.5 $\mu$M) was then added to the cells for 4 h, cell lysate was subjected to immunoblotting to measure the phosphorylation levels of $p42/44^{MAPK}$ and MEK-1/2.

To assess the involvement of protein kinase C, HepG2 cells pretreated with various protein kinase C inhibitors were subjected to SB202190 treatments. It is interesting to note that highly selective protein kinase C inhibitors, calphostin C, Bis I, and Go6976 has no effect on SB202190-induced LDL receptor expression (FIG. 8A). Conversely, staurosporine, a non-specific inhibitor of various protein kinases, including protein kinase C, completely prevented induction of LDL receptor expression by SB202190. As expected, pretreatment of HepG2 cells with staurosporine blocked SB202190-induced $p42/44^{MAPK}$ and MEK-1/2 activation, further supporting the involvement of a staurosporine-sensitive step in $p42/44^{MAPK}$ activation (FIG. 8B).

Discussion

Although $p38^{MPAK}$ and $p42/44^{MAPK}$ are members of different mitogen-activated protein kinase subfamilies, the present invention provides an evidence for one-way crosstalk between these mitogen-activated protein kinases. The conclusions that SB202190-induced LDL receptor expression is due to inhibition of $p38^{MAPK}$, and this pathway exerts its effect on LDL receptor expression through $p42/44^{MAPK}$ activation, is based on the following observations. First, under experimental conditions where PD98059 completely inhibited phosphorylation of $p42/44^{MAK}$ this MEK-1/2 inhibitor blocked SB202190-induced LDL receptor expression. The selectivity of PD98059 has been described in several studies, and the possibility that SB202190 inhibits another $p38^{MAPK}$ is unlikely because this inhibitor is without effect even at higher concentrations (100 µM) on either $p46/54^{JNK}$, or $p42/44^{MAPK}$, or multiple other related protein kinases including the homologues $p38^{MAPK}$ γ (SAPK3) and SAPK4, which share 60% identity with $p38^{MAPK}$ α and β.

The present invention also demonstrated that both PD980569 and SB202190 failed to block other mitogen-activated protein kinases in vivo at concentrations that completely blocked $p38^{MAPK}$ activity (43). Furthermore, to rule out the possibility that SB202190may inhibit other unknown targets to fully execute its effect on $p42/44^{MAPK}$ and LDL receptor expression, it is shown that expression of MKK6b(E), the constitutive activator of $p38^{MAPK}$, significantly suppressed LDL receptor promoter activity (FIG. 3). The effect of MKK6b(E) was dependent on activation of $p38^{MAPK}$, since coexpression of MKK6b with $p38^{MAPK}$, but not the inactive $p38^{MAPK}$ (AF) mutant, inhibited LDL receptor expression. Finally, consistent with the role of $p42/44^{MAPK}$ in SB202190-induced LDL receptor expression, inhibition of $p38^{MAPK}$ resulted in induction of its activity in a time-dependent manner. Activation of both the $p42/44^{MAPK}$ and LDL receptor expression was observed with similar kinetics suggesting that the activated $p42/44^{MAPK}$ is required to continuously increase the expression of the LDL receptor gene. $p42/44^{MAPK}$ phosphorylation started at 4 hours, with a maximal activation observed after 8 hours, and remained persistent up to 24 hours following treatment with SB202190. This delay in SB202190-induced $p42/44^{MAPK}$ is most likely due to the late appearance of an immediate or downstream substrate of the $p38^{MAPK}$ pathway either through de novo synthesis, post-translational modification or localization. The finding that SB202190-induced LDL receptor induction is not inhibited by cycloheximide (FIG. 7), a protein synthesis inhibitor, rules out de novo synthesis. It is more likely that induction of $p42/44^{MAPK}$ by SB202190 requires post-translational modification of the already existing substrate(s). Moreover, the lack of effect of sterols on SB202190-induced $p42/44^{MAPK}$ activation supports the notion that the sterol-sensitive step either lie downstream of $p42/44^{MAPK}$ or is a part of an independent signaling pathway.

This study represents the first demonstration of a functional difference observed for $p38^{MAPK}$ isoforms in the regulation of gene expression. Recent evidence indicates the existence of at least four distinct isoforms of $p38^{MAPK}$; $p38^{MAPK}$ α, also named CSBP2 or stress-activated protein kinase 2a; $p38^{MAPK}$ β, also named stress-activated protein kinase 2b and its splice isoform β2, $p38^{MAPK}$ γ, also termed stress-activated protein kinase 3 or ERK6; and $p38^{MAPK}$ δ, otherwise known as stress-activated protein kinase 4. The four isoforms are similar in size, show about 60 to 75% sequence homology, and are all activated by TNF, IL-1, ultraviolet radiation, and hyperosmolar medium. Some isoforms show a pronounced preference in tissue expression and selective interaction with upstream kinases and downstream substrates, pointing to highly specialized functions. These isoforms also differ in susceptibility to inhibition by SB202190; both α- and β-isoforms of $p38^{MAPK}$ are inhibited by SB202190, whereas the γ and δ isoforms are insensitive (26). Therefore, it seems less likely that either the γ or the δ isoform is responsible for the induction of LDL receptor expression by SB202190.

Since hepatic cells contain similar levels of $p38^{MAPK}$ α- and β-isoforms, next question to be asked is which of the isoform is responsible for the SB202190-induced LDL receptor expression in HepG2 cells. Availability of expression vectors encoding the individual $p38^{MAPK}$ isoforms made it possible to directly test their involvement by co-transfection studies. It was found that, unlike $p38^{MAPK}$ β-isoform, expression of the $p38^{MAPK}$ α-isoform suppressed LDL receptor promoter activity. These studies suggest that SB202190-induced LDL receptor expression is mediated by the inhibition of α-isoform of $p38^{MAPK}$ The observed difference in the role of α- and β-isoforms is consistent with a recent report that showed opposite effects of these isoforms on SB202190-induced apoptosis (54).

At this point, it is not clear why the α- and not the β-isoform negatively controls LDL receptor expression via $p42/44^{MAPK}$. One possibility is that these two $p38^{MAPK}$ isoforms may differ in their substrate specificity, and such differences could allow coupling of $p38^{MAPK}$ α-isoform to the $p42/44^{MAPK}$ signaling pathway. In an attempt to elucidate the mechanism underlying this cross-talk, various inhibitors of protein kinase C were used. It is interesting to note that staurosporine completely blocked SB202190-induced $p42/44^{MAPK}$ activation (FIG. 8). Staurosporine was originally considered to be a specific inhibitor of protein kinase C, but further studies revealed it also inhibits a variety of tyrosine kinases as well as serine-threonine kinases (55).

The role of protein kinase C in SB202190-induced LDL receptor expression is ruled out by the lack of effects of specific PKC inhibitors on the induction process. At this point, it is not clear which protein kinase is inhibited by staurosporine, but it is safe to predict that cross-talk between $p42/44^{MAPK}$ and $p38^{MAPK}$ pathways clearly requires signaling via a staurosporine-sensitive protein kinase that lie upstream of MEK-1/2. Because the number of substrates for $p38^{MAPK}$ that have been characterized in any system is few, and those that might contribute to activation of $p42/44^{MAPK}$ pathways have not been explored, this remains a question for future endeavors.

The suppression of $p42/44^{MAPK}$ activity that is initiated by $p38^{MAPK}$ activation provides a critical link in the signaling events preceding apoptosis. The ability of stressful signals to stimulate $p38^{MAPK}$ activity has led to the suggestion that this pathway may function to communicate growth inhibitory and apoptotic signals within the cell. $p38^{MAPK}$ is involved in the regulation of apoptosis, since overexpression of kinases that can activate $p38^{MAPK}$ resulted in the induction of apoptosis (56, 57), and inhibition of $p38^{MAPK}$ activity has been shown to suppress apoptosis (58). However, simple transient activation of the stress kinase cascades is not always sufficient to induce apoptosis. For example, TNF promotes a significant induction of $p46/54^{JNK}$ and $p38^{MAPK}$ but does not invariably induce apoptosis through induction of caspases (59). In this regard, it was suggested that concomitant inactivation of survival signals may be a prerequisite for $p46/54^{JNK}$ and $p38^{MAPK}$ to induce cell death (60). Interestingly, deprivation of neurotrophic factors in PC-12 cells or ultraviolet-irradiation of NIH-3T3 cells not only activates the stress kinase cascades but also leads to a dramatic inhibition of the $p42/44^{MAPK}$ pathway (56, 61). In fact, overexpression of $p42/44^{MAPK}$ in NIH-3T3 cells impaired a large part of the ultraviolet-induced apoptotic response (61). Furthermore, inhibition of $p42/44^{MAPK}$ alone has been shown to induce apoptosis through activation of caspases (62).

The negative regulation of $p42/44^{MAPK}$ by the $p38_{MAPK}$ is consistent with the above results and provides a critical link between the $p38^{MAPK}$ activation and the concomitant inhibition of $p42/44^{MAPK}$ signaling cascade. It is likely that induction of apoptosis due to $p38^{MAPK}$ activation could be at least partly due to inhibition of the $p42/44^{MAPK}$. The contradiction regarding the role of $p38^{MAPK}$ in apoptosis may be due to differences in the degree and extent of cross-talk between the "death" signal mediated by $p38^{MAPK}$ and the survival signal generated by activation of $p42/44^{MAPK}$, and the differential responses may lead to outcome in a cell- and stimuli-specific manner. Such a mechanism may reconcile the contradictory roles that have been suggested for $p38^{MAPK}$ in apoptosis.

Figure 9:
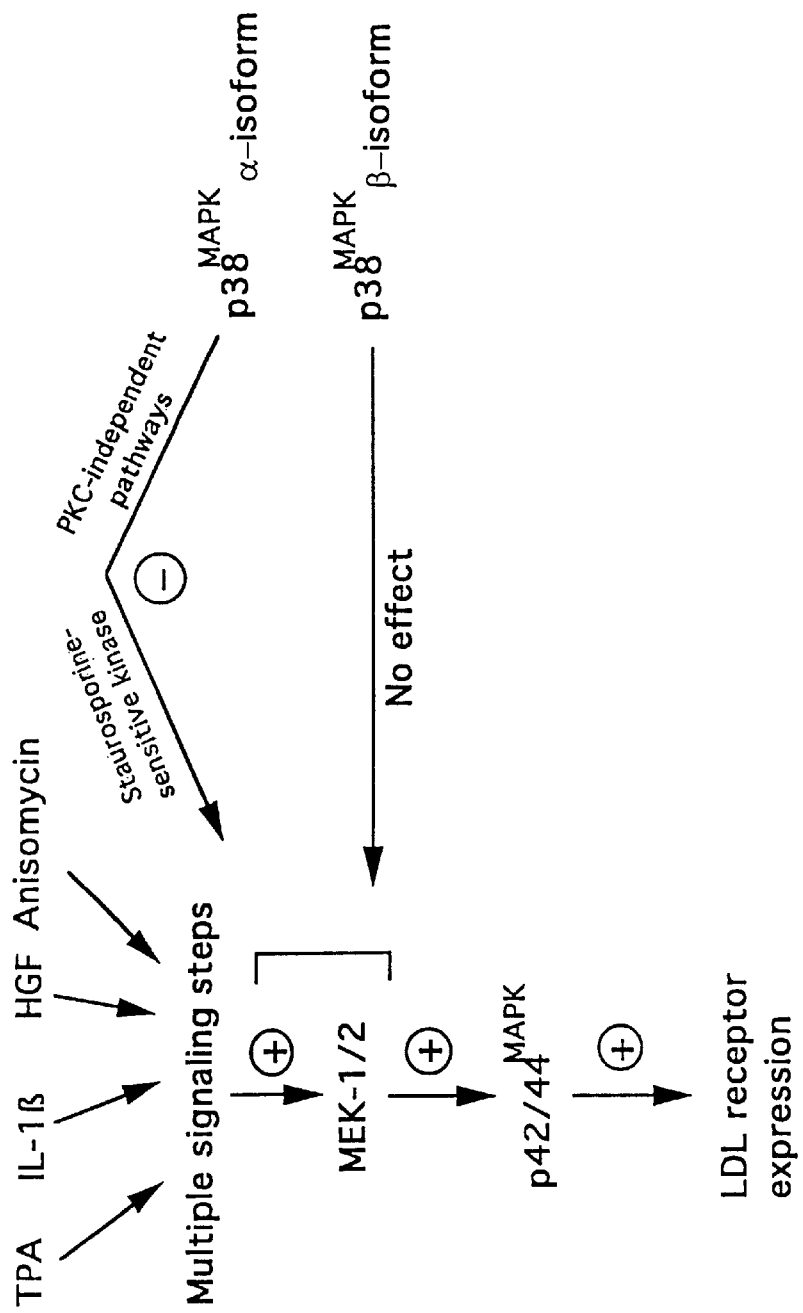
FIG. 9 shows a suggested model for cross-talk between $p38^{MAPK}$ and $p42/44^{MAPK}$ signaling pathways for regulating LDL receptor expression.

In conclusion, while studying the role of $p38^{MAPK}$ in the regulation of LDL receptor expression, a one-way inhibitory cross-talk was unraveled between the $p42/44^{MAPK}$ and $p38^{MAPK}$ signaling pathways. In conjunction with earlier work (43–45), the above results demonstrate that both $p38^{MAPK}$ and $p42/44^{MAPK}$ signaling pathways are important in regulating LDL receptor expression in intact cells. A signal transduction cascade involving $p42/44^{MAPK}$ and $p38^{MAPK}$ has been proposed to account for SB202190-induced LDL receptor induction by a staurosporine-sensitive protein kinase (FIG. 9). The signaling cascade leading top $42/44^{MAPK}$ activation is still not known and might involve a complex combinatorial, spatial cross-talk of already synthesized messenger molecules. The interplay between these signaling cascades should be an important process and dynamic balance may be critical for determining the outcome of a wide array of biological processes. Elucidation of the signaling components involved in this communication will significantly advance the ability to design novel strategies for the treatment of hypercholesterolemia and for understanding other important pathophysiological processes.

The following references were cited herewith.
1. Marshall, C. J. (1995) Cell 80: 179–185
2. Seger, etval., FASEB (1995) 9,726–735
3. Whitmarsh, et al., (1996) J. Mol. Med. 74: 589–607
4. Robinson, et al., (1997) Curr. Opin. Cell Biol. 9, 1805.
5. Davis, (1994) Trends Biochem. Sci. 19: 470–473
6. Cano, et al., (1995) Trends Biochem. Sci. 20, 117–122
7. Cobb, et al., (1995) J. Biol. Chem. 270: 14843–14846
8. Khokhlatchev, et al., (1997) J. Biol. Chem. 272: 11057–11062
9. Wood, et al., (1992) Cell 68: 1041–1050
10. Howe, et al., (1992) Cell 71: 335–342
11. Kyriakis, et al., (1994) Nature 369: 156–160
12. Derijard, et al., Cell 76: 1025–1037
13. Minden, et al., (1994) Mol. Cell. Biol. 14: 6683–6688
14. Raingeaud, et al., (1995) J. Biol. Chem. 270: 7420–7426
15. Han, et al., (1994) Science 265: 808–811
16. Gupta, et al., (1996) EMBO J. 15: 2760–2770
17. Lee, et al., (1994) Nature 372, 739–746.
18. Rouse, et al., (1994) Cell 78: 1027–1037.
19. Jiang, et al., (1996) J. Biol. Chem. 271: 17920–17926
20. Lechner, et al., (1996) Proc. Natl. Acad. Sci. U.S.A. 93: 4355–4359.
21. Li, et al., (1996) Biochem. Biophys. Res. Commun. 228: 334–340
22. Mertens, et al., (1996) FEBS Lett. 383: 273–276
23. Cuenda, et al., (1997) EMBO J. 16: 295–305
24. Wang, et al., (1997) J. Biol. Chem. 272: 23668–23674
25. Goedert, et al., (1997) EMBO J. 16: 3663–3671
26. Enslen, et al., (1998) J. Biol. Chem. 273: 1741–1748
27. Derijard, et al., (1995) Science 267: 682–685
28. Lin, et al., (1995) Science 268: 286–290
29. Sanchez, et al., (1994) Nature 372: 794–798
30. Moriguchi, et al., (1996) J. Biol. Chem. 271: 13675–13679
31. Holland, et al., (1997) J. Biol. Chem. 272: 24994–24998
32. Raingeaud, et al., (1996) Mol. Cell. Biol. 16: 1247–1255
33. Treisman, R. (1996) Curr. Opin. Cell. Biol. 8: 205–215
34. Pang, et al., (1995) J. Biol. Chem. 270, 13585–13588
35. Cuenda, et al., (1995) FEBS Lett. 364, 229–233
36. Beyaert, et al., (1996) EMBO J. 15: 1914-
37. Hazzalin, et al., (1996) Curr. Biol. 6: 1028-
38. Crawley, et al., (1997) J. Biol. Chem. 272: 15023-
39. Kawasaki, et al., (1997) J. Biol. Chem. 272: 18518-
40. Graves, et al., (1998) J. Immunol. 161: 168-
41. Tan, et al., (1996) EMBO J. 15: 4629-
42. Iordanov, et al., (1997) EMBO J. 16: 1009-
43. Kumar, et al., (1998) J. Biol. Chem. 273: 15742–15748
44. Kumar, et al., (1997) J. Lipid Res. 38, 4220–4228
45. Mehta, et al., (1999) J. Lipid Res., Manuscript submitted
46. Mehta, et al., (1996) J. Biol. Chem. 271: 33616–33622
47. Kramer, et al., (1996) J. Biol. Chem. 271: 27723–27729
48. Lee, et al., (1993) Ann. N. Y. Acad. Sci. 696: 149–170
49. Vane, J. R. (1971) Nat. New. Biol. 231: 232–235
50. Han, et al., (1996) J. Biol. Chem. 271: 2886–2891
51. Bosch, et al., (1997) Oncogene 15: 1021–1033
52. Woods, et al., (1997) Mol. Cell. Biol. 17: 5598–5611
53. Frasch, et al., (1998) J. Biol. Chem. 273: 8389–8397
54. Nemoto, et al., (1998) J. Biol. Chem. 273: 16415–15420
55. Meggio, et al., (1995) Europ. J. Biochem. 234: 317–322
56. Xia, et al., (1995) Science 270: 126–131
57. Ichijo, et al., (1996) Science 275: 90-
58. Schwenger, et al., (1997) Proc. Natl. Acad. Sci. U.S.A. 2869–2873
59. Liu, et al., (1996) Cell 87: 565–576.
60. Canman, et al., (1996) Nature 384: 213–214
61. Berra, et al., (1997) Mol. Cell. Biol. 17: 4346–4354
62. Berra, et al., (1998) J. Biol. Chem. 273: 10792–10797

Any patents or publications mentioned in this specification are indicative of the levels of those skilled in the art to which the invention pertains. These patents and publications are herein incorporated by reference to the same extent as if each individual publication was specifically and individually indicated to be incorporated by reference.

One skilled in the art will readily appreciate that the present invention is well adapted to carry out the objects and obtain the ends and advantages mentioned, as well as those inherent therein. The present examples along with the methods, procedures, treatments, molecules, and specific compounds described herein are presently representative of preferred embodiments, are exemplary, and are not intended as limitations on the scope of the invention. Changes therein and other uses will occur to those skilled in the art which are encompassed within the spirit of the invention as defined by the scope of the claims.

What is claimed is:

1. A method of inducing low density lipoprotein receptor expression in a cell consisting essentially of the step of:

administering a compound selected from the group consisting of the pyridinylimidazole compounds (4-(4-Fluorophenyl)2-(4-methylsulfinylphenyl)-5-(4-pyridyl)1H-imidazole) and (4-(4-Fluorophenyl)-2-(4-hydroxyphenyl)-5-(4-pyridyl) 1H-imidazole), wherein said compound activates mitogen-activated protein kinase $p42/44^{MAPK}$ by inhibiting the mitogen-activated protein kinase $p38^{MAPK}$.

2. The method of claim 1, wherein said cell is selected from the group consisting of a hepatic cell and a nonhepatic cell.

3. The method of claim 1, wherein said method further reduces cholesterol level in said cell.

4. A method of treating an individual having hypercholesterolemia, consisting essentially of the step of:

administering a compound selected from the group consisting of the pyridinylimidazole compounds (4-(4-Fluorophenyl)2-(4-methylsulfinylphenyl)-5-(4-pyridyl)1H-imidazole) and (4-(4-Fluorophenyl)-2-(4-hydroxyphenyl)-5-(4-pyridyl)1H-imidazole), wherein said compound activates mitogen-activated protein kinase $p42/44^{MAPK}$ by inhibiting the mitogen-activated protein kinase $p38^{MAPK}$.

5. The method of claim 4, wherein said compound is administered at a concentration range of from about 1 $\mu$M to about 100 $\mu$M.

* * * * *